US010099036B2

(12) United States Patent
Heideman et al.

(10) Patent No.: US 10,099,036 B2
(45) Date of Patent: Oct. 16, 2018

(54) STEERABLE CATHETER USING FLAT PULL WIRES AND HAVING TORQUE TRANSFER LAYER MADE OF BRAIDED FLAT WIRES

(71) Applicant: St. Jude Medical, Atrial Fibrillation Division, Inc., St. Paul, MN (US)

(72) Inventors: Wayne Heideman, Minnetonka, MN (US); Allan M. Fuentes, Mound, MN (US); Richard E. Stehr, Stillwater, MN (US); Sarah Cumming, Plymouth, MN (US); Mark Dustrude, Minnetonka, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 683 days.

(21) Appl. No.: 14/284,026

(22) Filed: May 21, 2014

(65) Prior Publication Data

US 2014/0303599 A1 Oct. 9, 2014

Related U.S. Application Data

(60) Continuation of application No. 12/861,555, filed on Aug. 23, 2010, now Pat. No. 8,734,699, which is a
(Continued)

(51) Int. Cl.
*A61M 25/00* (2006.01)
*A61M 25/01* (2006.01)

(52) U.S. Cl.
CPC ........ *A61M 25/01* (2013.01); *A61M 25/0012* (2013.01); *A61M 25/0147* (2013.01);
(Continued)

(58) Field of Classification Search
CPC ............ A61M 25/0147; A61M 25/005; A61M 25/0136; A61M 2025/015; A61M 25/0045
See application file for complete search history.

(56) References Cited

U.S. PATENT DOCUMENTS 4,306,029 A 12/1981 Carpenter
4,425,919 A 1/1984 Alston, Jr. et al.
(Continued)

FOREIGN PATENT DOCUMENTS

JP 2001178826 7/2001
WO 1997/001369 1/1997
(Continued)

OTHER PUBLICATIONS

International Search Report and Written Opinion for PCT/US07/68176 dated Jul. 23, 2008.
(Continued)

*Primary Examiner* — Emily Schmidt
(74) *Attorney, Agent, or Firm* — Wiley Rein LLP

(57) ABSTRACT

A catheter assembly includes an inner liner made of flexible material and an outer layer having a steering mechanism. The steering mechanism includes at least one flat wire and a corresponding lumen through which the flat wire may travel. The steering mechanism may also include at least one pull ring to which the flat wires are attached. A layer of heat shrink material may encompass the outer layer. A braided wire assembly may also be provided in the outer layer, and may be formed by braiding a plurality of flat wires into a wire mesh. The overall cross-section of the catheter assembly is preferably substantially circular. A catheter shaft may include a plurality of segments of differing hardness characteristics. The outer layer typically comprises a melt processing polymer such that the catheter assembly may be laminated using heat.

12 Claims, 11 Drawing Sheets

Related U.S. Application Data division of application No. 11/953,604, filed on Dec. 10, 2007, now abandoned, which is a continuation-in-part of application No. 11/647,313, filed on Dec. 29, 2006, now abandoned.

(60) Provisional application No. 60/800,373, filed on May 16, 2006.

(52) U.S. Cl.
CPC ..... *A61M 25/0045* (2013.01); *A61M 25/0053* (2013.01); *A61M 2025/015* (2013.01)

(56) References Cited

U.S. PATENT DOCUMENTS

| | | | |
|---|---|---|---|
| 4,686,963 A * | 8/1987 | Cohen | A61B 1/0055 138/120 |
| 4,899,787 A | 2/1990 | Ouchi et al. | |
| 5,125,895 A | 6/1992 | Buchbinder et al. | |
| 5,125,896 A | 6/1992 | Hojeibane | |
| 5,238,005 A | 8/1993 | Imran | |
| 5,281,217 A | 1/1994 | Edwards et al. | |
| 5,395,328 A | 3/1995 | Ockuly et al. | |
| 5,395,329 A | 3/1995 | Fleischhaker et al. | |
| 5,472,017 A * | 12/1995 | Kovalcheck | A61B 1/0052 138/103 |
| 5,487,757 A | 1/1996 | Truckai et al. | |
| 5,782,828 A | 7/1998 | Chen et al. | |
| 5,843,031 A | 12/1998 | Hermann et al. | |
| 5,843,152 A | 12/1998 | Tu et al. | |
| 5,861,024 A | 1/1999 | Rashidi | |
| 5,876,340 A | 3/1999 | Tu et al. | |
| 5,891,138 A | 4/1999 | Tu et al. | |
| 5,893,884 A | 4/1999 | Tu | |
| 5,897,554 A | 4/1999 | Chia et al. | |
| 5,906,605 A | 5/1999 | Coxum | |
| 5,941,845 A | 8/1999 | Tu et al. | |
| 5,951,471 A | 9/1999 | de la Rama et al. | |
| 5,954,651 A | 9/1999 | Berg et al. | |
| 6,023,638 A | 2/2000 | Swanson | |
| 6,029,091 A | 2/2000 | de la Rama et al. | |
| 6,033,403 A | 3/2000 | Tu et al. | |
| 6,143,013 A | 11/2000 | Samson et al. | |
| 6,212,426 B1 | 4/2001 | Swanson | |
| 6,233,477 B1 | 5/2001 | Chia et al. | |
| 6,241,727 B1 | 6/2001 | Tu et al. | |
| 6,308,090 B1 | 10/2001 | Tu et al. | |
| 6,450,948 B1 | 9/2002 | Matsuura et al. | |
| 6,582,536 B2 | 6/2003 | Shimada | |
| 6,942,661 B2 | 9/2005 | Swanson | |
| 6,991,616 B2 * | 1/2006 | Bencini | A61M 25/0147 600/585 |
| 2001/0049491 A1 | 12/2001 | Shimada | |
| 2002/0077590 A1 | 6/2002 | Ponzi et al. | |
| 2002/0123749 A1 | 9/2002 | Jain | |
| 2002/0177772 A1 | 11/2002 | Altman et al. | |
| 2004/0122360 A1 | 6/2004 | Waldhauser et al. | |
| 2004/0143256 A1 | 7/2004 | Bednarek | |
| 2004/0181208 A1 | 9/2004 | Poole | |
| 2005/0038467 A1 | 2/2005 | Hebert et al. | |
| 2005/0107737 A1 | 5/2005 | McDaniel | |
| 2005/0267461 A1 | 12/2005 | Cao et al. | |
| 2007/0005008 A1 | 1/2007 | Honebrink et al. | |
| 2007/0173757 A1 * | 7/2007 | Levine | A61M 25/008 604/95.04 |
| 2007/0270679 A1 | 11/2007 | Nguyen et al. | |

FOREIGN PATENT DOCUMENTS

| | | |
|---|---|---|
| WO | 1999/033509 | 7/1999 |
| WO | 2001/078825 | 10/2001 |
| WO | 2005/065584 | 7/2005 |
| WO | 2007/136981 | 11/2007 |

OTHER PUBLICATIONS

International Search Report and Written Opinion for PCT/US08/83241 dated Mar. 3, 2009.

* cited by examiner

STEERABLE CATHETER USING FLAT PULL WIRES AND HAVING TORQUE TRANSFER LAYER MADE OF BRAIDED FLAT WIRES

CROSS-REFERENCE TO RELATED APPLICATIONS

This application is a continuation of U.S. application Ser. No. 12/861,555, filed 23 Aug. 2010, which is a divisional of U.S. application Ser. No. 11/953,604, filed 10 Dec. 2007, which is a continuation-in-part of U.S. application Ser. No. 11/647,313, filed 29 Dec. 2006, which claims the benefit of U.S. provisional application No. 60/800,373, filed 16 May 2006. Each of the foregoing is incorporated by reference as though fully set forth herein.

BACKGROUND OF THE INVENTION a. Field of the Invention

The present invention pertains generally to catheters that are used in the human body. More particularly, the present invention is directed to steerable catheters using flat pull wires to reduce the overall outer dimension of the catheter and a torque transfer layer made of braided flat wires and configured to provide increased strength, flexibility, and kink resistance.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. The catheter typically carries one or more electrodes, which may be used for ablation, diagnosis, or the like.

Many prior catheters use round wires as pull wires, and they typically either embed the wire directly into the catheter wall so that the pull wire and the lumen through which it runs are substantially the same size, or use a round wire to create a pull wire lumen and then place a smaller wire in the lumen as a pull wire. These conventional techniques and methods result in a catheter that is elliptical in its outer shape. An example of an elliptical catheter is disclosed and taught in U.S. Pat. No. 6,582,536, the contents of which are incorporated herein by reference.

As catheters are used in smaller and smaller passages, there is a growing need to use catheters that have a smaller outer dimension. Accordingly, there is a need to use steerable catheters that have smaller cross-sections.

It is known that, to facilitate placement of the diagnostic or therapeutic catheter at a location of interest within the patient, it may be introduced through another catheter, commonly known as a "guiding catheter" or "introducer catheter," and the terms will be used interchangeably herein. Generally speaking, an introducer catheter is a tube having a high degree of directional control that is used to place other catheters, which may have little or no directional control, into specific areas of the patient's body.

In the field of cardiac ablation, for example, introducer catheters may be used to negotiate the patient's vasculature such that an ablation device may be passed therethrough and positioned to ablate arrhythmia-causing cardiac tissue. The introducer catheter itself may be advanced over a guide wire.

Generally, it is known that the introducer catheter must have an overall diameter small enough to negotiate blood vessels while retaining an inner diameter (or "bore size") large enough to accommodate the ablation device therethrough. Furthermore, since the path within the patient is often long and tortuous, steering forces must be transmitted over relatively great distances. Accordingly, it is desirable for the introducer catheter to have sufficient axial strength to be pushed through the patient's vasculature via a force applied at its proximal end ("pushability"). It is also desirable for the introducer catheter to transmit a torque applied at the proximal end to the distal end ("torqueability"). An introducer catheter should also have sufficient flexibility to substantially conform to the patient's vasculature and yet resist kinking as it does so. One of ordinary skill in the art will recognize that these various characteristics are often in tension with one another, with improvements in one requiring compromises in others. For example, increasing the bore size of an introducer catheter having a given overall diameter requires utilizing a thinner wall. A thin-walled introducer, however, is more likely to collapse upon itself when a torque is applied at its proximal end.

To improve pushability, torqueability, flexibility, and kink resistance, many extant introducer catheters utilize one or more reinforcing layers in their construction. For example, the guiding catheter disclosed in U.S. Pat. No. 4,817,613 to Jaraczewski et al. ("Jaraczewski") includes a pair of braided torque transmitting layers sandwiched between a flexible tubular member and a flexible plastic casing applied as a viscous material and subsequently cured. Jaraczewski also teaches, however, that to a certain degree, flexibility comes at the expense of torqueability. Further, depending on the thickness of the torque transfer layers, they may increase the wall thickness, thereby either increasing the overall diameter of the introducer catheter for a given bore size or decreasing the bore size for a given overall diameter.

Many extant large bore introducers (i.e., an introducer catheter with bore size of greater than about 6 French), in order to find a suitable balance of pushability, torqueability, flexibility, and kink resistance, have outer layers that are relatively stiff, which compromises torqueability, kink resistance, and flexibility for pushability.

BRIEF SUMMARY OF THE INVENTION

According to a first embodiment of the invention, a catheter assembly includes an inner liner made of flexible material and an outer layer having a steering mechanism. The steering mechanism includes at least one flat wire and a corresponding lumen for each of the at least one flat wire through which the flat wire may travel. Optionally, the catheter assembly may include a layer of heat shrink material encompassing the outer layer, a central lumen, and/or a braided wire assembly contained in the outer layer. The overall cross-section of the catheter assembly may be substantially circular. The outer layer typically comprises a melt processing polymer such that the catheter assembly may be laminated using heat.

Optionally, the flat wire or wires may be encased in a preformed tube in which the flat wire may travel. The flat wire may have a rectangular cross-section, typically having dimensions of about X by about 3X, and the cross-section of the preformed tube may be oval, round, or elliptical. That is, the cross-section of the preformed tube may be of a different shape than the cross-section of the flat wire disposed therein. The flat wire may be coated with a lubricious substance to permit the flat wire to slide in its lumen, or optionally, the flat wire may be manufactured with a smooth surface to reduce friction between the flat wire and its lumen.

The braided wire assembly may extend from a base of the catheter assembly to a distal end of the catheter assembly, and a braid density may transition from a first braid density at the base to a lower braid density at the distal end. For example, the braid density may be about 50 PPI at the base and about 10 PPI at the distal end. Alternatively, the braid density at the distal end may be about 20% to about 35% of the braid density at the base.

Also disclosed is a method of manufacturing a catheter including the steps of: providing a mandrel; placing a lining material over the mandrel to form an inner liner; providing at least one flat shaped wire; placing a flexible liner over each of the at least one flat shaped wires to create at least one flat lumen; placing a braided wire assembly over the inner liner and the at least one flat lumen; covering the braided wire assembly with a melt processing polymer; applying sufficient heat to the melt processing polymer to raise the temperature of the polymer above its melting point; cooling the assembly; and removing the mandrel, thereby forming a catheter. Typically, the catheter is manufactured such that it has a cross-section with an outer shape that is substantially circular with an outer diameter of less than about 12 F. Optionally, the melt processing polymer may be covered with shrink wrap tubing to help promote the polymer flowing through the braided wire assembly. The shrink wrap tubing may be left in place after manufacturing, or it may be removed as part of the manufacturing process. The melt processing polymer is typically selected from Nylon, PEBAX and other thermal elastomers. Optionally, additional layers of melt processing polymers may be placed over the flat lumen and the inner liner. Typically, the flat wire and the flexible liner being placed over the flat wire will each have different cross-sectional shapes.

Also disclosed is a method of manufacturing a steerable introducer catheter, including the steps of: providing a mandrel; laminating the mandrel with a lining material to form an inner liner; providing at least one flat shaped wire; covering the inner liner and the at least one flat shaped wire with a melt processing polymer; applying sufficient heat to the melt processing polymer to raise the temperature of the polymer above its melting point; cooling the assembly; and removing the mandrel, thereby forming a steerable introducer catheter. Optionally, a flexible tube is placed over each of the at least one flat shaped wires to create at least one corresponding lumen for each of the wires, and further, the melt processing polymer may be covered with a layer of shrink wrap tubing. The braided wire assembly may be characterized by a braid density that transitions from a first number at the base to a lower number at the tip. The variation in braid density may range from about 50 PPI at the base to about 10 PPI at the distal end.

In accordance with another aspect of the present invention, a catheter or an introducer catheter for cardiac surgery comprises a tubular inner liner, a torque transfer layer, or reinforcing layer, surrounding at least a portion of the inner liner, the torque transfer layer comprising at least two flat wires braided into a wire mesh, and an outer sheath formed over to the torque transfer layer. The flat wires are substantially rectangular in cross-section and have a width of at least about 0.007 inches and a depth of at least about 0.003 inches. The tubular inner liner has a lumen diameter of at least about 6 French. In specific embodiments, the catheter is an introducer catheter. The tubular inner liner is polymeric and the outer sheath comprises a melt-processing polymer. The ratio of width to thickness of the introducer catheter may be between about 2:1 and about 5:1. The torque transfer layer has a braid density of between about 5 PPI and about 100 PPI and may be braided in a one-over, one-under pattern, or a two-over, two-under pattern. The outer sheath comprises a plurality of segments having differing hardness characteristics, and the segments are reflow bonded together.

The catheter assembly of the present invention may also include a pull ring to which the at least two flat wires are secured. The pull ring may be a right circular cylinder having a slot for each of the at least two flat wires. Typically, there are two flat wires, the pull ring has two slots spaced on opposite sides of the pull ring, and each of the flat wires is secured in the slot by a laser weld. The pull ring may further include at least two flow holes such that the outer layer will bond to the pull ring during melt processing as the melt processing polymer flows through the flow holes and then becomes rigid after cooling.

The catheter assembly of the present invention may also include a shaft made of at least three segments, wherein each segment has a different hardness characteristic. For example, a first shaft segment may be made of nylon, a second segment may be made of a first PEBAX, and a third segment may be made of a second PEBAX that is more flexible than both the nylon and the first PEBAX. Additional segments may be used to form the shaft, each of which may have greater or lesser degrees of stiffness.

Also disclosed is a pull ring assembly for a catheter including a pull ring having at least one rectangular slot and at least one flat pull wire, wherein each of the at least one flat pull wires is secured to the at least one rectangular slot of the pull ring. Typically, the pull ring assembly will include at least two slots and at least two flat pull wires secured in the slots. Optionally, the pull ring may include flow holes though which a melt processing polymer may flow during lamination.

According to still another embodiment of the invention, a pull ring assembly includes a pull ring having at least two rectangular slots and at least two pull wires, wherein each of the at least two pull wires is secured to the rectangular slot of the pull ring. Optionally, the pull ring may include flow holes though which a melt processing polymer may flow during lamination.

A technical advantage of the present invention is that overall cross-section of the catheter may be reduced.

Another technical advantage of the present invention is that a steerable catheter using flat pull wires may be provided that enjoys greater flexibility.

Yet another technical advantage of the invention is it may utilize an improved braided wire assembly that provides for greater flexibility and control of a catheter.

A further technical advantage of the invention is that a method of manufacturing an improved steerable catheter is provided.

Yet another technical advantage of the invention is that a catheter shaft having greater flexibility and control may be utilized.

A further technical advantage of the invention is that a method of manufacturing an introducer with a lower profile outer diameter with improved steerability is provided.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 13 depicts an inner layer disposed over a reflow mandrel assembly in accordance with a preferred method of manufacture.

DETAILED DESCRIPTION OF THE INVENTION

Flat Pull Wires

The present invention provides an improved steerable catheter that minimizes the overall outer dimensions by utilizing a variety of improved techniques. One technique is to utilize flat wire as the pull wires for the steerable catheter.

For purposes of this invention, a "flat wire" or a "flat pull wire" refers to a wire that is characterized by a cross-section that, when measured along two orthogonal axes, is substantially flat. A flat wire typically has a rectangular cross-section. For example, the rectangular cross-section may be approximately 0.004" by 0.012". The cross-section need not be perfectly rectangular. For example, the present invention contemplates a cross-section of the flat wire may be oval, provided that the overall cross-section is generally flat. For example, a wire may be properly characterized as a flat wire if it has a cross-section that is measured X in one direction and at least 3X in a second direction generally orthogonal to the first direction. A wire whose cross-section is substantially I-shaped may also be a flat wire if, generally, its height is substantially greater than its width at its widest measurement. One of ordinary skill will appreciate that a flat wire may be defined in the context of the overall teachings of this application.

The use of a flat wire as a pull wire also has the added benefit that it provides greater resistance to deflection in certain directions. The shape of a round wire is not predisposed to resist deflection in any particular direction, whereas the shape of a flat wire will be predisposed to resist deflection on a first axis, and yet predisposed to permit deflection on a second axis that is orthogonal to the first axis. Thus, by using a pull wire that is not circular, a catheter can be predisposed to permit and favor deflection in one direction over another.

The outer diameter of the catheter may also be minimized at the distal tip by an improved braided wire assembly. In particular, a braid may be used that is characterized by a varying braid density from the proximal end to the distal tip. Preferably, the braid is less dense at the tip than at the proximal end of the catheter. Some applications may be better suited if the braid density is more dense at the tip than at the proximal end, while other applications may be better suited if the braid density is greater on both ends than in the middle of the catheter.

Figure 1:
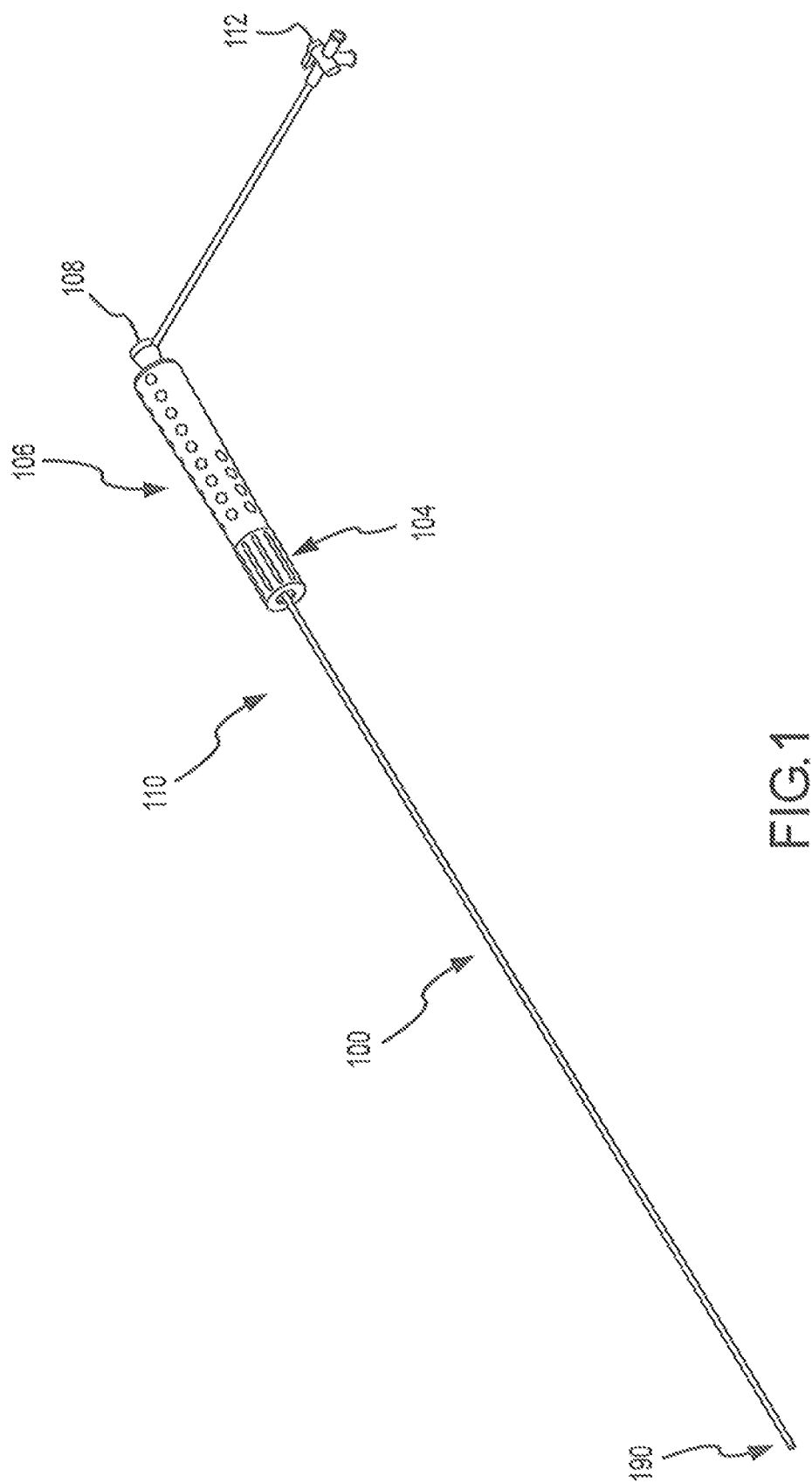
FIG. 1 is perspective view of an embodiment of a catheter of the present invention.

FIG. 1 is a perspective view of a catheter assembly 110 according to one embodiment of the present invention comprising a catheter or an introducer catheter 100 having a proximal portion 104 and a distal portion 190. The catheter 100 may be operably connected to a handle assembly 106 which assists in guiding or steering the introducer during procedures. The catheter assembly 110 further includes a hub 108 operably connected to an inner lumen (not shown) within the handle assembly 106 for insertion or delivery of catheter assemblies, fluids, or any other devices known to those of ordinary skill in the art. Optionally, the catheter assembly 110 further includes a valve 112 operably connected to the hub 108.

Figure 2:
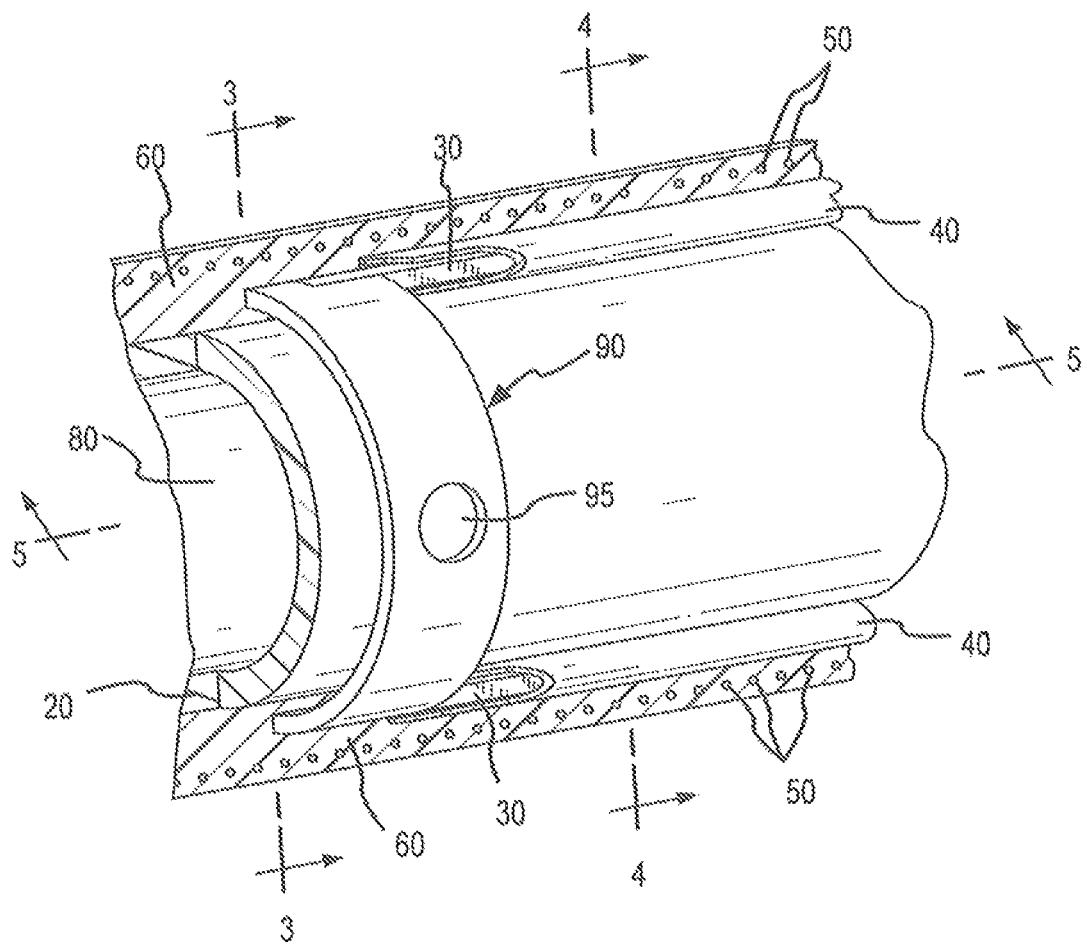
FIG. 2 illustrates a perspective view of a section of a catheter according to an embodiment of the present invention, cut away to show details.

FIG. 2 illustrates a perspective view of a catheter according to a preferred embodiment of the present invention, cut away to show details.

The basic method of manufacture of catheter 100 according to an embodiment of the present invention will be described with reference to FIGS. 2, 3, 4, 6, 7 and 8. As they are assembled, the catheter components will be collectively referred to as a catheter assembly.

Figure 6:
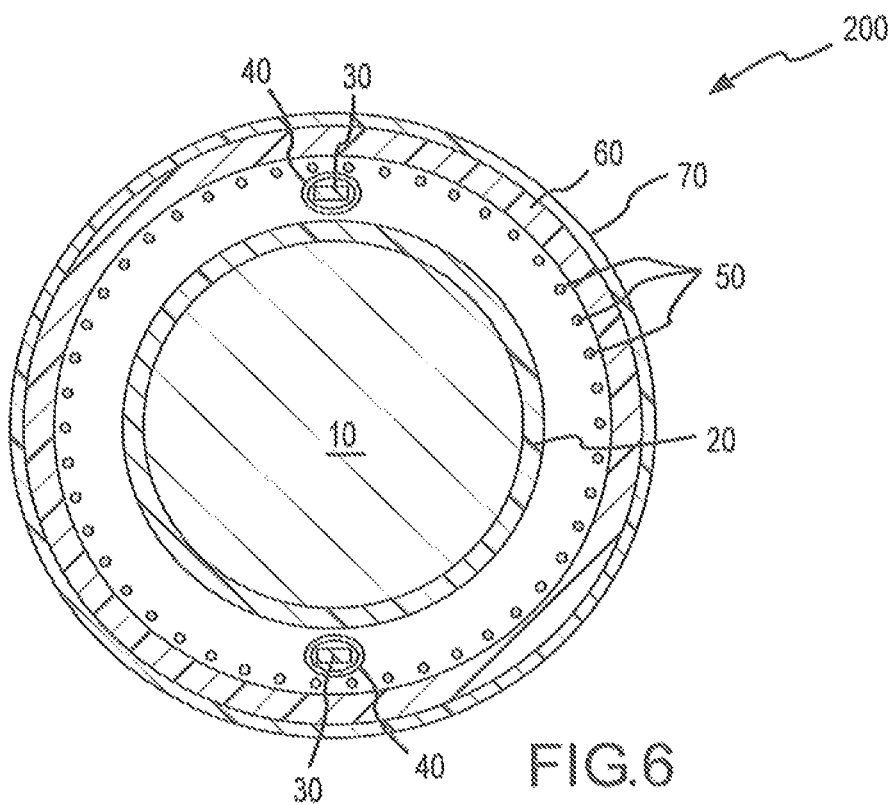
FIG. 6 is a cross-sectional view of a catheter assembly prior to the application of heat to melt process the outer layer.

As depicted in FIG. 6, a mandrel 10, which is preferably round in cross-section and preferably from about 6 inches to about 4 feet in length, is a component of the catheter assembly 200, and may be the first component thereof during manufacture of catheter 100. Mandrel 10 has a distal end and a proximal end. An inner liner 20 is placed on mandrel 10. Inner liner 20 may be knotted at one end (e.g. the distal end) and then fed onto mandrel 10.

Preferably, inner liner 20 is an extruded polytetrafluoroethylene (PTFE) tubing, such as TEFLON® brand tubing, which is available commercially Inner liner 20 may also be made of other melt processing polymers, including, without limitation, etched polytetrafluoroethylene, polyether block amides, nylon and other thermoplastic elastomers. Once such elastomer is PEBAX®, made by Arkema, Inc. PEBAX of various durometers may be used, including, without limitation, PEBAX 30D to PEBAX 70D. In a preferred embodiment, inner liner 20 is made of a material with a melting temperature higher than that of an outer layer 60, which will be further described below, such that inner liner 20 will withstand melt processing of outer layer 60.

A flat wire 30 is placed longitudinally along inner liner 20. Flat wire 30 is preferably composed of stainless steel and is preferably about 0.002" by about 0.016", and more preferably about 0.004" by about 0.012". In one embodiment, at least a portion of flat wire 30 is encased inside another preformed tube 40 before placement along inner liner 20 to form a flat lumen 42. Preformed tube 40 need not have the same shape as the cross-section of flat wire 30, but instead may be round, oval, rectangular, or another like shape. Preferably, preformed tube 40 has a cross-section that is not the same shape as the cross-section of flat wire 30 in order to facilitate movement of flat wire 30 in preformed tube 40. Preformed tube 40 may be formed of polytetrafluoroethylene, polyether block amides, nylon, other thermoplastic elastomers, or another substance. Preferably, preformed tube 40 has a higher melting point than outer layer 60, which will be further described below, so that preformed tube 40 will not melt when outer layer 60 is subjected to melt processing.

In alternative embodiments, flat wire 30 may be covered with lubricious materials including silicone, TEFLON® (PTFE), siloxane, and other lubricious materials (not shown), before placement. Alternatively, flat wire 30 may also be coated with a lubricious layer to promote slideability. It is also contemplated that flat wire 30 may be manufactured with a smooth surface to promote slideability. While stainless steel is a preferred material from which to compose flat wire 30, other materials may be used, including, without limitation, materials that are used for conventional round pull wires.

More than one flat wire 30 may also be used. In such cases, each such flat wire 30 may be encased inside its own flexible tube 40 to form separate flat lumens 42. Preferably, a pair of flat wires 30 are used, spaced apart about 180 degrees about the circumference of inner liner 20.

Outer layer 60 is then placed over inner liner 20, flat wires 30, and preformed tube 40 forming flat lumen 42. Outer layer 60 may be made of either single or multiple sections of tubing that may be either butted together or overlapped with each other. Preferably, outer layer 60 is an extruded polytetrafluoroethylene tubing, such as TEFLON® brand tubing, which is available commercially. Outer layer 60 may also be made of other melt processing polymers, including, without limitation, etched polytetrafluoroethylene, polyether block amides, nylon and other thermoplastic elastomers. Once such elastomer is PEBAX® made by Arkema, Inc. PEBAX of various durometers may be used, including, without limitation, PEBAX 30D to PEBAX 70D. Outer layer 60 may also comprise more than one layer, including for example two or more tubes of a melt processing polymer.

Optionally, a braided wire assembly 50 may be placed over inner liner 20 and any flat wires 30 before outer layer 60 is applied. Braided wire assembly 50 may be formed of stainless steel wire, including for example 0.003" high tensile stainless steel wire. Braided wire assembly 50 may be formed in a standard braid pattern and density, for example, about 16 wires at about 45 to about 60 picks per inch ("PPI") density. Alternatively, a braid may be used that is characterized by a varying braid density. For example, braided wire assembly 50 may be characterized by a first braid density at proximal end 104 of catheter 100 and then transition to one or more different braid densities as braided wire assembly 50 approaches distal end 190 of catheter 100. The braid density of distal end 190 may be greater or less than the braid density at proximal end 104. In a specific example, the braid density at the base (i.e., proximal end 104) is about 50 PPI and the braid density at distal end 190 is about 10 PPI. In another embodiment, the braid density at distal end 190 is about 20% to about 35% of the braid density at the base/proximal end 104.

Braided wire assembly 50 may be formed separately on a disposable core. One or more portions of braided wire assembly 50 may be heat tempered and cooled before incorporation into catheter assembly 200 though methods that are known to those of ordinary skill. The action of heat tempering may help to release the stress on the wire and help reduce radial forces.

FIG. 6 displays a cross-section of catheter assembly 200 having two flat wires 30 and braided wired assembly 50 encompassed by outer layer 60 before lamination of the materials by heating. In one preferred embodiment, a layer of heat shrink 70 is placed over the top of outer layer 60 as depicted in FIG. 6. Heat shrink 70 is preferably a fluoropolymer or polyolefin material.

Figure 7:
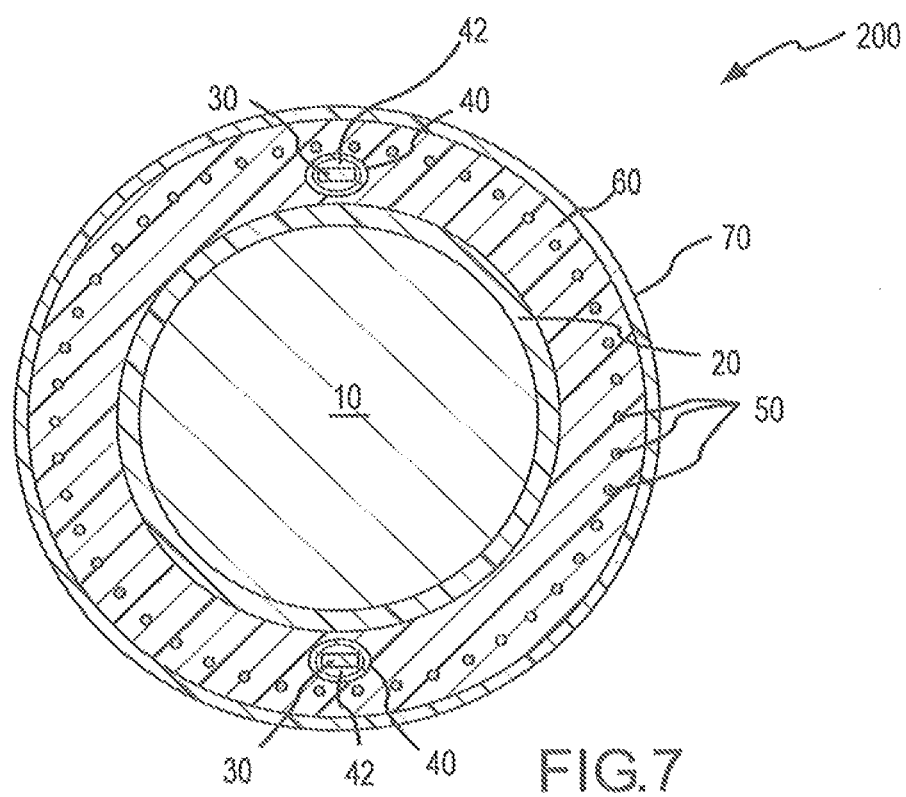
FIG. 7 is a cross-sectional view of a catheter after the application of heat to melt process the outer layer.

FIG. 7 depicts catheter assembly 200 after a lamination process. Catheter assembly 200 may be laminated by heating catheter assembly 200 until the material comprising outer layer 60 flows and redistributes around the circumference thereof as depicted in FIG. 7. Heat shrink 70 has a higher melting temperature than outer layer 60; and during the melt process, heat shrink 70 retains its tubular shape and forces the liquefied outer layer 60 material into braided wire assembly 50 (if present) and into contact with flat wires 30 and inner liner 20. Catheter assembly 200 may then be cooled. In FIG. 7, mandrel 10 is still in place.

Figure 4:
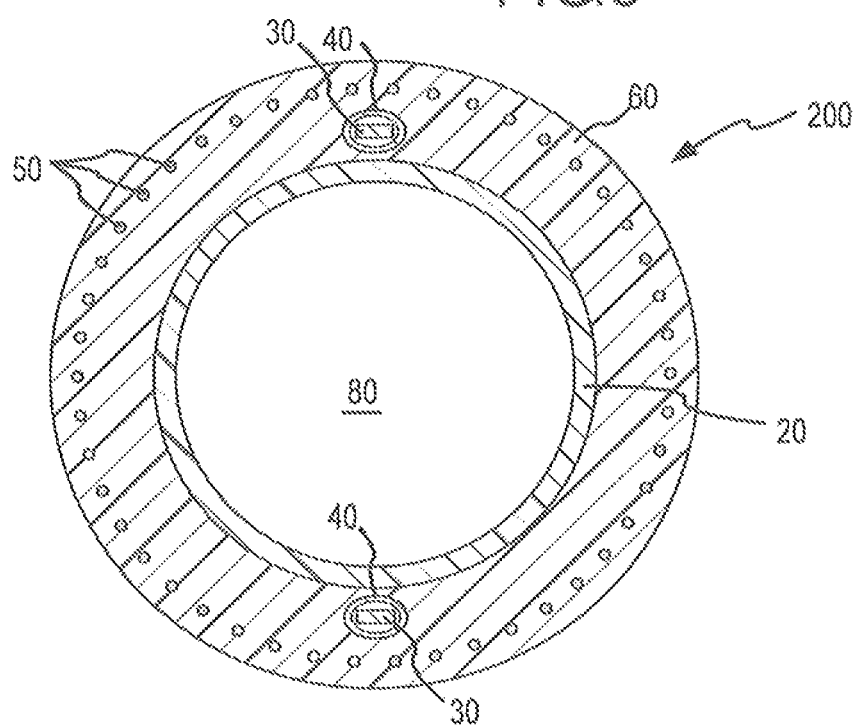
FIG. 4 is a cross-sectional view taken along line 4-4 in FIG. 2.

Mandrel 10 may be removed from catheter assembly 200, leaving behind a lumen 80 as illustrated in FIG. 4, which depicts a catheter 100 made in accordance with the method of the present invention subsequent to the application of heat for the lamination process. Optionally, heat shrink 70 may be left in place around outer layer 60, as depicted in FIG. 7, even after mandrel 10 is removed.

Figure 3:
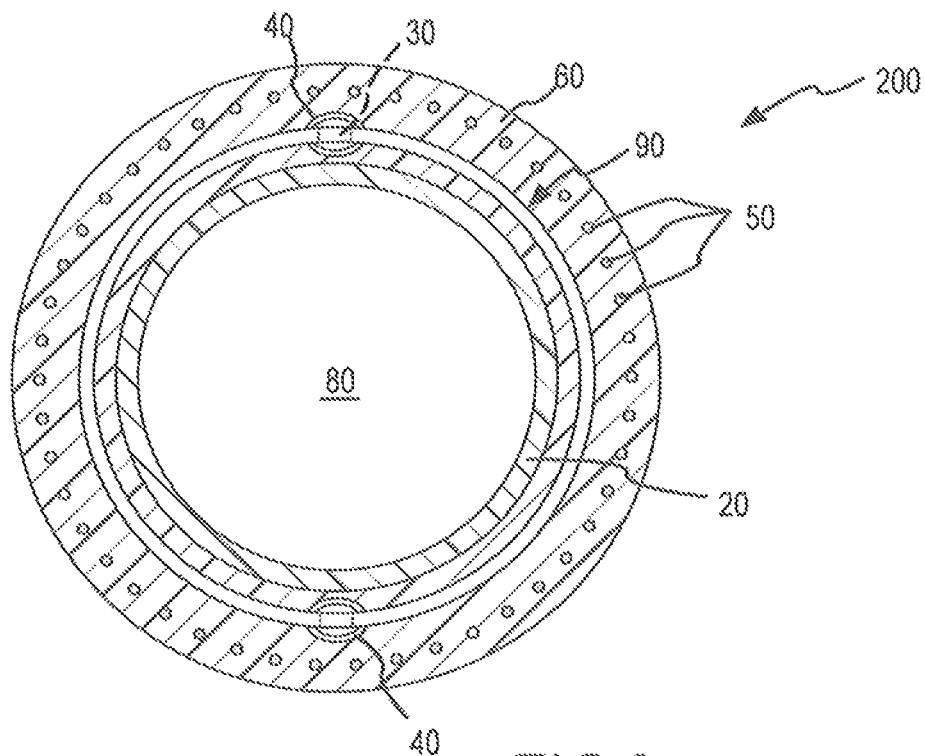
FIG. 3 is a cross-sectional view taken along line 3-3 in FIG. 2.
Figure 8:
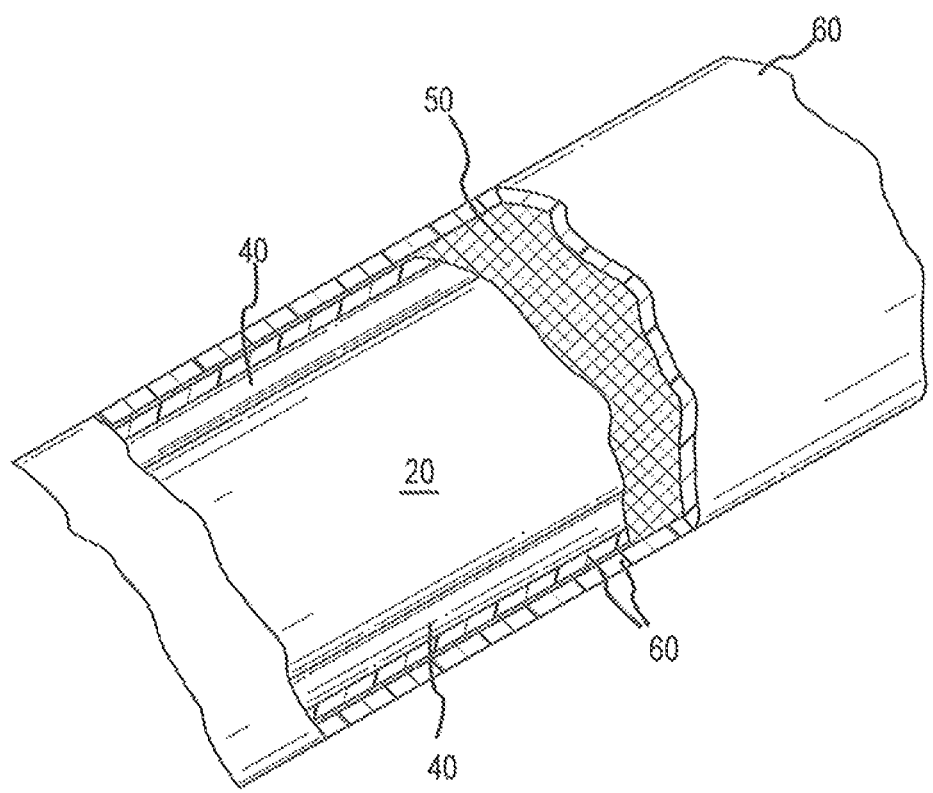
FIG. 8 illustrates a perspective view of a partially assembled catheter in accordance with another embodiment of the invention, cut away to show details.

If heat shrink 70 is removed, outer layer 60 becomes the outermost layer of catheter 100. The result is a substantially circular catheter 100 with pull wires 30 embedded within outer layer material as illustrated in FIGS. 3 and 4. FIG. 3 is a cross-sectional view taken at the point of a pull ring 90 as depicted in FIG. 2, while FIG. 4 is a cross-sectional view taken at a point proximal to pull ring 90. FIG. 8 is a perspective view of catheter assembly 200, cut away to show certain details of construction.

Catheter assembly 200 may be manufactured using alternative techniques. In one embodiment, outer layer 60 may be formed by extruding outer layer 60 over catheter assembly 200. In another embodiment, catheter assembly 200 may formed by using a combination of heat and a press that has a mold for defining the final shape of catheter 100.

Catheter 100 formed using the methods of this invention may have varying sizes and various uses. For example, catheter 100 may be used in atrial fibrillation cases as well as atrial tachycardia cases. In connection with certain heart applications, catheter 100 manufactured using the improvements discussed herein is preferably less than about 12 F outer diameter, and more preferably less than about 10 F outer diameter. For use as a steerable introducer, a catheter size of less than about 11 F outer diameter may be preferred. As discussed below, larger catheter sizes are feasible, particularly when the torque transfer layer is made of braided flat wires.

In another embodiment, catheter 100 construction may be modified to utilize materials of various durometer hardness (as measured, for example, using a Shore durometer hardness scale). For example, proximal end 104 of catheter 100 may be made of a material such as nylon 11, and the remainder of catheter 100 may be made of one or more PEBAX materials. Preferably, the durometer hardness levels will decrease as catheter 100 shaft approaches distal end 190. For example, a nylon base may then be followed by one or more of the following PEBAX segments: 70D PEBAX; 60D PEBAX; 55D PEBAX; 40D PEBAX; 35D PEBAX; 30D PEBAX. Catheter 100 may also use one or more blends of the foregoing PEBAX materials, including for example, a 70D/60D PEBAX blend made by co-extrusion, or a 40D/35D PEBAX blend made by co-extrusion. Preferably, catheter 100 made with one or more segments of varying durometers will be reflowed together during manufacturing. The length of the segments may vary. Proximal end 104 of catheter 100 is preferably the longest segment, and more distal segments may preferably vary between about 0.25" to about 6", and more preferably from about 0.25" to about 3". Preferably, the hardness levels of the segments and the lengths of the segments may be adjusted for specific applications, and preferably, the distal tip segment may have the lowest durometer of all segments. The segments may be selected to optimize stability and torque delivery for the specific application.

Figure 5:
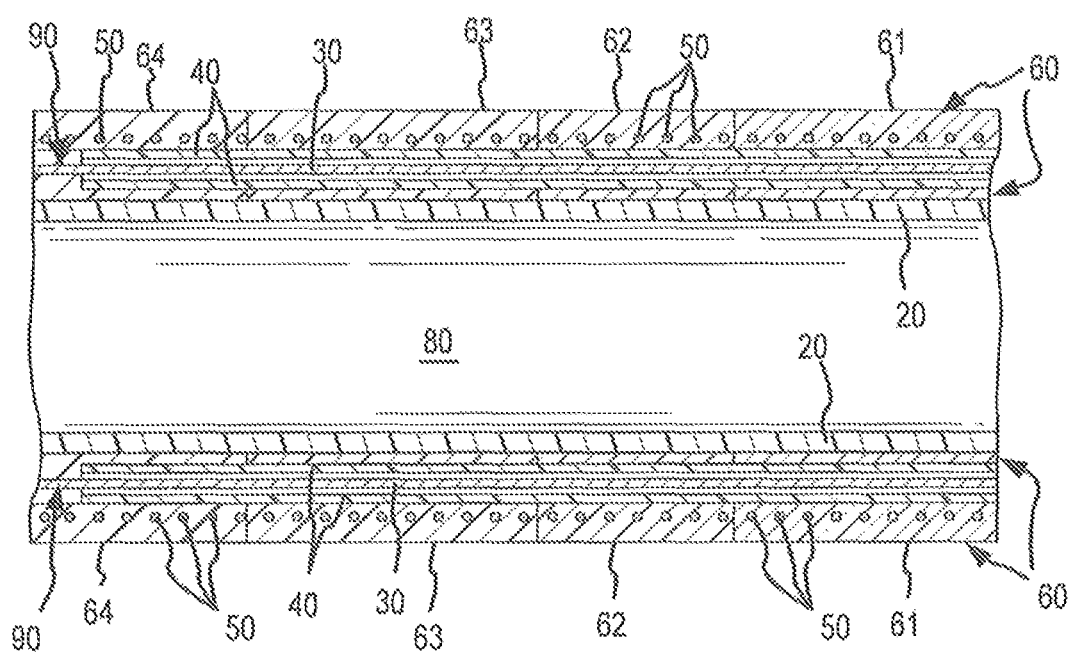
FIG. 5 is a cross-sectional view taken along line 5-5 in FIG. 2.

FIG. 5 illustrates another embodiment of the invention in which outer layer 60 is composed of multiple segments 61, 62, 63, 64, each of which has different material properties, such as degree of hardness, stiffness, or tensile strength. In a preferred embodiment, segment 61 has the greatest degree of hardness; segments 62, 63, and 64 are more flexible than segment 61; segments 63 and 64 are more flexible than segments 61 and 62; and finally, segment 64 is more flexible than each of segments 61, 62 and 63. The number of segments may vary, as well as the relative lengths of the segments.

In yet another embodiment, a modified braided wire assembly 50 is inserted between inner liner 20 and outer layer 60. Braided wire assembly 50 may be designed to have transitional braid densities starting at one braid density and transitioning to a lower braid density. In one embodiment, the braid may begin at a braid density of about 50 to about 60 PPI, and more preferably between about 50 and about 55 PPI, and then transition to a braid density at the tip of about 5 to about 20 PPI, and more preferably between about 5 to about 15 PPI. The braid density may transition slowly, or it may change using one or more segments. For example, there may be an intermediate zone with a braid density of about 30 to about 45 PPI. Variations in the braid density of braided wire assembly 50 may be used to increase or decrease flexibility of catheter 100 depending on the desired application.

Figure 9:
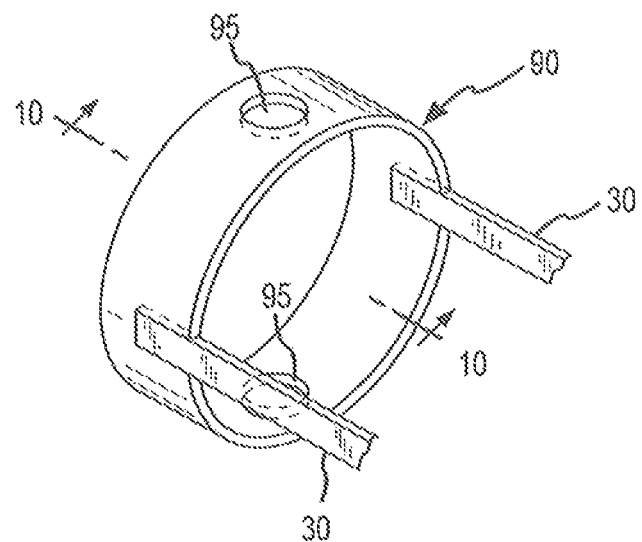
FIG. 9 illustrates a pull ring that may be used in a catheter according to the present invention.
Figure 10:
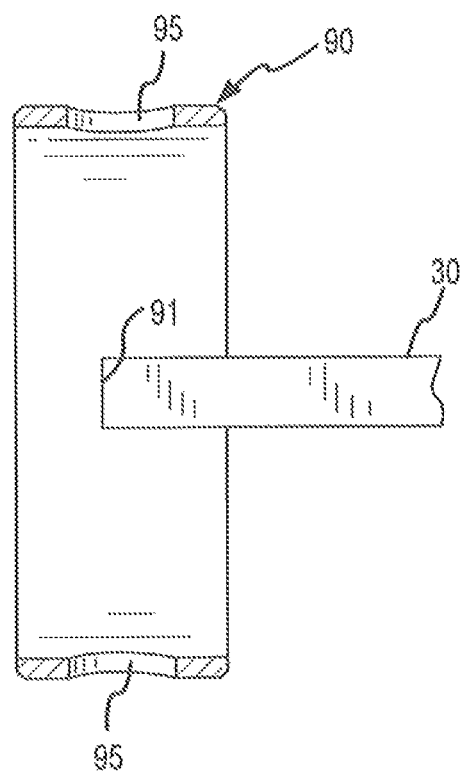
FIG. 10 is a sectional view of the pull ring of FIG. 9 taken along line 10-10.

In another embodiment, pull ring 90 is utilized to provide steerability. FIGS. 9 and 10 illustrate a preferred embodiment for pull ring 90. Pull ring 90 is a generally circular band with a cross-sectional shape (measured orthogonally to a tangential line relative to the circle of the band) that is substantially rectangular. The rectangular cross-section is more clearly depicted in FIG. 10. The outer dimension of pull ring 90 is preferably determined based on the application for catheter 100 to be manufactured. In one embodiment, pull ring 90 is about 0.10" in diameter.

Pull ring 90 preferably has at least one slot 91 that is configured to accommodate flat pull wire 30. Flat pull wire 30 may secured within slot 91 by any technique that is appropriate given the materials of pull ring 90 and flat pull wires 30. Acceptable techniques may include, but are not limited to, laser welding and/or other welding and bonding techniques.

In another embodiment, pull ring 90 may contain one or more flow holes 95 as illustrated in FIGS. 9 and 10. During a melting process, the material of outer layer 60 melts and flows through flow holes 95. Upon cooling, the material of outer layer 60 bonds to pull ring 90 to provide better adhesion between pull ring 90 and the remaining components of catheter assembly 200, thereby improving performance of catheter 100. While flow holes 95 are depicted as circular, other shapes may be used. In one embodiment, pull ring 90 includes two 0.025" flow holes 95 spaced about 180 degrees apart around the circumference of pull ring 90. The size and shape of flow holes 95 may be adjusted based on the materials being used to form inner liner 20 and/or outer layer 60.

In another embodiment, pull ring 90 is utilized with non-flat pull wires. Pull ring 90 of this embodiment is preferably a circular band with a cross-sectional shape (measured orthogonally to a tangential line relative to the circle of the band) that is substantially rectangular. Preferably, pull ring 90 has at least one slot that is configured to accommodate a non-flat pull wire (such as a round wire). Preferably, the tip of the non-flat pull wire is tapered to facilitate joinder with pull ring 90. The non-flat pull wire may be secured within the slot by any technique that is appropriate given the materials of pull ring 90 and the pull wires. Acceptable techniques may include, but are not limited to, laser welding and/or other welding and bonding techniques. Preferably, the non-flat pull wire is located within a preformed tube. The preformed tube need not be the same shape as the cross-section of the pull wire, but instead, may be round, oval, rectangular, or another like shape. Preferably, the preformed tube has a cross-section that is not the same shape as the cross-section of the pull wire in order to facilitate movement of the pull wire in the preformed tube. The preformed tube may be formed of polytetrafluoroethylene, polyether block amides, nylon, other thermoplastic elastomers or another substance. Preferably, the preformed tube has a higher melting point than outer layer 60 so that the preformed tube will not melt when outer layer 60 is subjected to melt processing. In alternative embodiments, the pull wire may be covered with lubricious materials, such as silicone and other lubricious materials, before placement. Alternatively, the pull wire may be coated with a lubricious layer to promote slideability, and it is also contemplated that the pull wire may be manufactured with a smooth surface to promote slideability. While stainless steel is a preferred material to compose the pull wire, other materials may be used, including, without limitation, materials that are used for conventional pull wires.

Pull ring 90 is typically utilized near distal end 190 of catheter 100, but it is anticipated that pull ring 90 may be located at any position along catheter 100. Moreover, more than one pull ring 90 may be utilized in the same catheter 100. In one embodiment of catheter 100, two separate pull rings 90 may be utilized, each of which has its own flat pull wires 30 connected thereto.

Although multiple embodiments of this invention have been described above with a certain degree of particularity, those skilled in the art could make numerous alterations to the disclosed embodiments without departing from the spirit or scope of this invention. For example, pull ring 90 may be made of stainless steel or other materials, including, without limitation, materials that are used to form conventional pull ring assemblies. In addition, braided wire assembly 50 may be made of stainless steel or other materials, including materials that are used to form conventional braided wire assemblies.

Torque Transfer Layer Using Braided Flat Wires

The present invention further provides a torque transfer layer using braided flat wires for a catheter and a large bore introducer catheter. For purposes of description, embodiments of the present invention will be described in connection with a flat wire guided, or steerable, introducer catheter. It is contemplated, however, that the described features may be incorporated into any number of catheters or introducer catheters as would be appreciated by one of ordinary skill in the art. The large bore introducer catheter is comprised of a combination of components and manufactured by either a reflow process or an extrusion process, which provide the surprising benefits of allowing for introducer catheters having an internal diameter of at least about 6 French while maintaining the desirable improved properties of pushability, torqueability, and flexibility, for outer diameters of sufficient size for navigation of cardiac vasculature.

Figure 11:
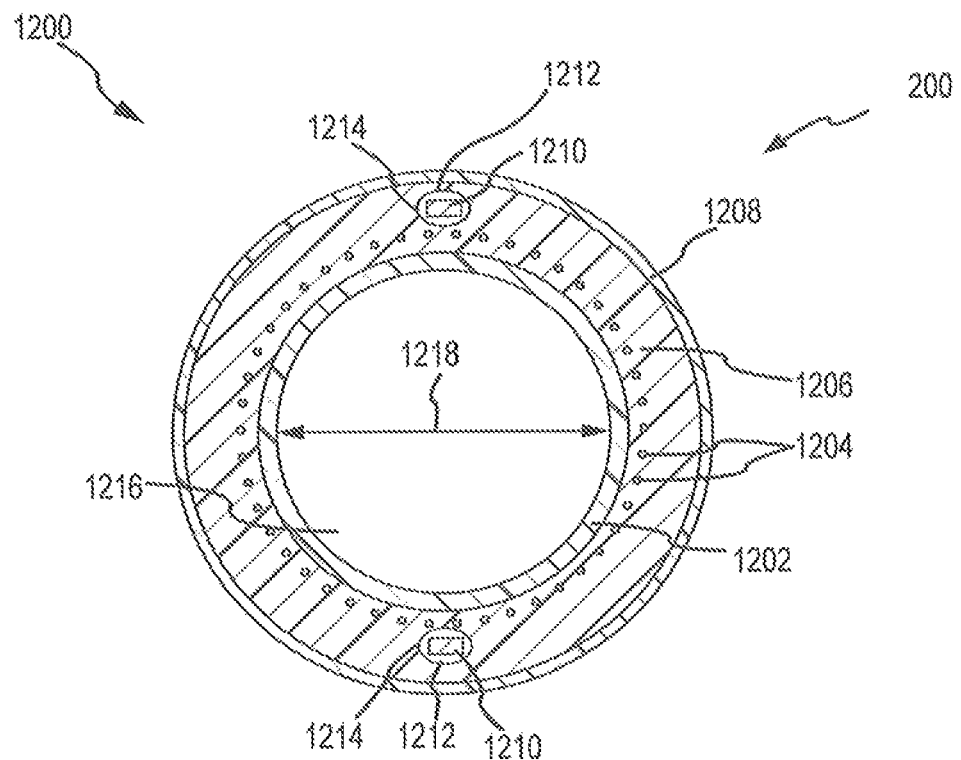
FIG. 11 is a cross-sectional view of a steerable, large bore introducer in accordance with another embodiment of the present invention.

FIG. 11 depicts a cross-sectional view of an introducer catheter 1200 in accordance with one embodiment of the present invention. The introducer catheter 1200 is comprised of a tubular polymeric inner liner 1202, a torque transfer layer 1204, an outer sheath 1206 comprised of a melt-processing polymer, and a heat shrink layer 1208. In the instance where the introducer is a steerable introducer, the introducer catheter 1200 further includes at least one flat wire 1210 disposed longitudinally along the length of the introducer catheter 1200. For purposes of this invention, a "flat wire" refers to a wire that is characterized by a cross-section that, when measured along two orthogonal axes, is substantially flat. A flat wire typically has a rectangular cross section, though the cross section need not be perfectly rectangular. For example, the present invention contemplates that a cross section of the flat wire may be oval, provided that the overall cross section is generally flat. As the term is used herein, a wire may be properly characterized as a flat wire if it has a cross section that is measured x in one direction and at least 2x in a second direction generally orthogonal to the first direction. A wire whose cross section is substantially I-shaped may also be a flat wire if, generally, its height is substantially greater than its width at its widest measurement. One of ordinary skill will appreciate that a flat wire may be defined in the context of the overall teachings of this application.

The at least one flat wire 1210 may be further encased inside another polymeric tubular member 1212 forming a lumen 1214 for housing the flat wire 1210. The introducer catheter according to this embodiment is manufactured by a reflow bonding process in which the components are individually fed over a mandrel as discussed in more detail below.

The inner liner 1202 is preferably a polymeric material, such as polytetrafluoroethylene (PTFE) or etched PTFE. The inner liner 1202 may also be made of other melt processing polymers, including, without limitation, polyether block amides, nylon and other thermoplastic elastomers. Once such elastomer is PEBAX® made by Arkema, Inc. PEBAX of various durometers may also be used, including without limitation, PEBAX 30D to PEBAX 70D. In a preferred embodiment, the inner liner 1202 is made of a material with a melting temperature higher than the outer sheath 1206 such that the inner liner 1202 will withstand the melt processing of the outer sheath 1206.

Inner liner 1202 defines a lumen 1216 therethrough, preferably having a diameter 1218 of at least about 6 French, more preferably of at least about 7 French, and most preferably of between about 10 French and about 24 French. However, in some embodiments of the invention, it is contemplated that lumen 1216 may have a diameter 1218 of up to about 32 French or more, such as between about 7 French and about 32 French.

A torque transfer layer 1204 is preferably disposed between the inner liner 1202 and the heat shrink layer 1208, more preferably between the outer sheath 1206 and the inner liner 1202. In the instance where the introducer is a steerable introducer utilizing, for example, at least one longitudinal wire 1210, the torque transfer layer 1204 may be disposed either between the inner layer 1202 and the outer sheath 1206 or between the outer sheath 1206 and the heat shrink layer 1208. The torque transfer layer 1204 may be made of stainless steel (304 or 316) wire or other acceptable materials known to those of ordinary skill in the art.

The torque transfer layer 1204 is preferably formed of a braided wire assembly comprised of flat wires, preferably stainless steel wires including, for example, high tensile stainless steel wires. The torque transfer layer 1204 may be formed in any number of known braid patterns, including one-over-one (involving at least two wires) or two-over-two (involving at least four wires) crossover patterns. The braided flat wires typically have a thickness of at least about 0.0005" and a width of at least about 0.005". Examples of larger sizes include 0.001" by 0.005" and 0.002" by 0.006". For lumen diameters of at least about 6 French, braided flat wires of at least about 0.003" thick by at least about 0.007" wide, which heretofore were not used to form a wire mesh for the torque transfer layer, have produced surprisingly good results of increased pushability, torqueability, flexibility, and kink resistance over non-flat wires and smaller flat wires. In general, the individual wires have a ratio of width to the thickness of at least about 2:1, including, for example, 2:1 to 5:1. Flat wires of about 0.004" thick by about 0.012" wide and of about 0.004" thick by about 0.020" wide have also been braided with success to form torque transfer layers of superior performance.

The braid density, commonly measured in pixels per inch ("PPI"), is typically between about 5 and 100, and will depend on the size of the flat wires as well as the size of the catheter. For flat wires of at least about 0.003" thick by about 0.007" wide and a catheter having an inner lumen of at least about 6 French, the PPI is preferably between about 10 and about 90, more preferably between about 10 and about 55. For example, the PPI for flat wires of about 0.003" thick by about 0.007" wide is preferably between about 20 and about 90, more preferably between about 35 and about 55 for an inner lumen of at least 6 French, and most preferably between about 35 and about 45 for an inner lumen of at least about 10 French. The PPI for flat wires of about 0.004" thick by about 0.012" wide is preferably between about 15 and about 70, and more preferably between about 15 and about 22 for an inner lumen of at least about 6 French. The PPI for flat wires of about 0.004" thick by about 0.020" wide is preferably between about 5 and about 50, and more preferably between about 10 and about 20 for an inner lumen of at least about 6 French, and most preferably between about 10 and about 20 for an inner lumen of at least about 16 French.

Alternatively, the torque transfer layer 1204 may utilize a varying braid density construction along the length of the introducer catheter 1200. For example, the torque transfer layer may be characterized by a first braid density at the proximal end of the introducer catheter 1200 and then transition to one or more braid densities as the torque transfer layer 1204 approaches the distal end of the introducer catheter 1200; the braid density of the distal end may be greater or less than the braid density at the proximal end. In a specific example, the braid density at the proximal end is about 50 PPI and the braid density at the distal end is about 10 PPI. In another embodiment, the braid density at the distal end is about 20-35% of the braid density at the proximal end.

The torque transfer layer 1204 may be formed separately on a disposable core and subsequently slipped around the inner liner 1202. One or more portions of the torque transfer layer 1204 may be heat tempered and cooled before incorporation into the introducer body 1200 through methods that are known to those of ordinary skill. The action of heat tempering may help to release the stress on the wire and help reduce radial forces. It is also contemplated that torque transfer layer 1204 may be braided directly on the inner liner 1202.

A particularly preferred torque transfer layer 1204 is comprised of 0.003" by 0.007" 304 stainless steel wires at 35 PPI for an inner lumen of 6-10 French. Another preferred torque transfer layer 1204 is comprised of 0.004" by 0.012" 304 stainless steel wires at 22 PPI for an inner lumen of 12 French. Yet another preferred torque transfer layer 1204 is comprised of 0.004" by 0.020" 304 stainless steel wires at 13 PPI for an inner lumen of 16 French. These particularly preferred torque transfer layers may manufactured on a commercially available horizontal braid machine set at 225 rpm utilizing a commercially available mandrel. Other suitable methods of manufacturing the torque transfer layer 1204 will be apparent to those of ordinary skill in the art.

Figure 15:
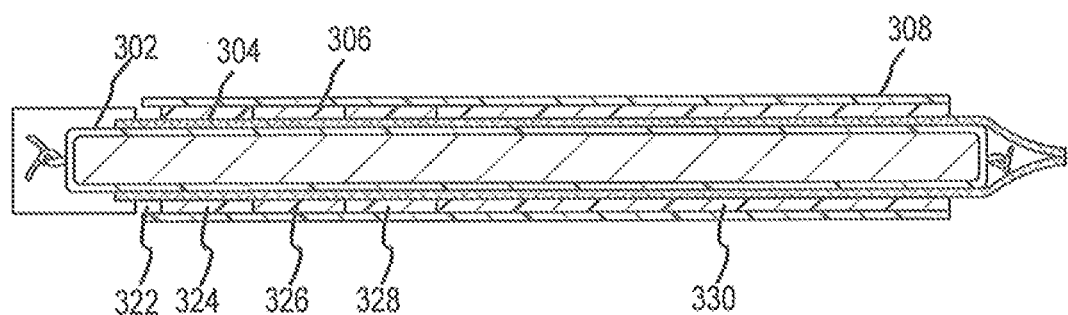
FIG. 15 depicts an outer sheath of varying components disposed over a torque transfer layer in accordance with a preferred method of manufacture.

The outer sheath 1206 is preferably either an extruded PEBAX or PTFE tubing. The melt-processing polymer of the outer sheath 1206 occupies a plurality of voids of the wire mesh in the torque transfer layer. The outer sheath 1206 may also be made of other melt processing polymers, including, without limitation, etched PTFE, polyether block amides, nylon and other thermoplastic elastomers, at varying durometers. The outer sheath 1206 may also comprise more than one layer, including, for example, two or more tubes of a melt processing polymer. Alternatively, as shown in FIG. 15, the outer sheath 306 may be comprised of varying segments 322, 324, 326, 328, 330 differing in hardness and/or material along the length of the introducer 300 and being reflow bonded together. This may be accomplished by layering or by placing annular rings of differing materials along the length of the introducer 300. Varying the sheath composition in this manner provides the additional benefit of adjusting flexibility, torqueability, and pushability at various points along the introducer 300.

In embodiments where the introducer is a steerable introducer (as shown in FIG. 11), at least one flat wire 1210 is provided, preferably extending along substantially the entire length of the introducer. The flat wire 1210 is preferably composed of stainless steel and is preferably about 0.002" by about 0.016", and more preferably about 0.004" by about 0.012" or 0.016". The flat wire may be selected such that the ratio of the width to thickness is at least about 2:1. In one embodiment, at least a portion of the flat wire is encased inside a preformed tube 1212 before placement along the inner liner 1202 to form a flat lumen 1214. The preformed tube 1212 need not be the same shape as the cross section of the flat wire, but instead, may be round, oval, rectangular, or another like shape. Preferably, the preformed tube 1212 has a cross section that is not the same shape as a cross section of the flat wire 1210, in order to facilitate movement of the flat wire in the preformed tube. The preformed tube may be formed of PTFE, etched PTFE, polyether block amides (such as PEBAX), nylon, other thermoplastic elastomers, or any other known material to one of ordinary skill in the art. Preferably, the preformed tube 1212 has a higher melting point than the outer sheath 1206 so that the preformed tube 1212 will not melt when the introducer catheter 1200 is subjected to melt processing. In alternative embodiments the flat wire 1210 may be covered with lubricious materials (not shown) before placement, including silicone and other lubricious materials. Alternatively, the flat wire 1210 may also be coated with a lubricious layer to promote slideability, and it is also contemplated that the flat wire 1210 may be manufactured with a smooth surface to promote slideability. While stainless steel is a preferred material to compose the flat wire 1210, other materials may be used, including, without limitation, materials that are used for conventional round pull wires. More than one flat wire 1210 may also be used, and in such cases, each such flat wire 1210 may be encased inside its own flexible tube 1212. Preferably, as shown in FIG. 11, a pair of flat wires 1210 are used that are spaced at 180 degrees apart. The flat wires 1210 are preferably connected to at least one steering ring typically located near the distal end of the introducer (see, e.g., similar flat wires 30 connected to steering ring 90 in FIG. 2). The proximal ends of the flat wires 1210 are then operably connected to a steering mechanism (not shown) allowing for manipulation, or steering, of the introducer catheter 1200 during use.

Figure 12:
FIG. 12 depicts a reflow mandrel assembly used in the method of manufacturing introducers in accordance with the present invention.

The basic method of manufacture according to an embodiment of the present invention will be described in reference to FIGS. 12-18. As the various components are assembled, the introducer components will be collectively referred to as an introducer. As depicted in FIGS. 12-18, a mandrel 300, which is preferably round in cross-section and preferably from about 6 inches to about 4 feet in length, is provided. As depicted in FIG. 12, the mandrel 300 has a distal end 350 and a proximal end 352. As depicted in FIG. 13, an inner liner 302 is placed on the mandrel 300. The inner liner 302 is fed on to the mandrel 300 and is then knotted on one end 320, or both ends.

Figure 14:
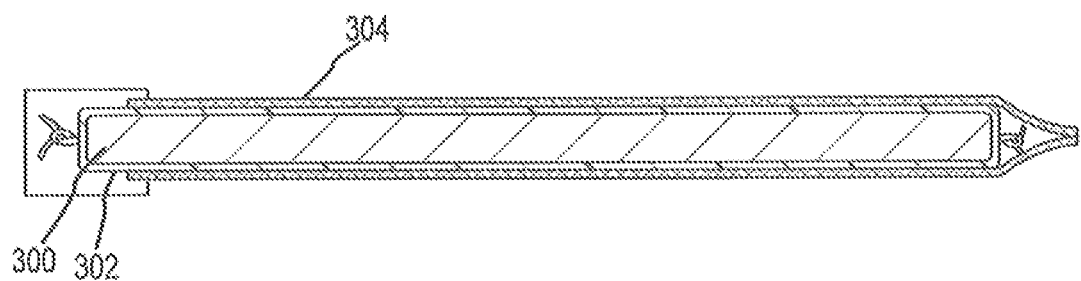
FIG. 14 depicts a torque transfer layer disposed over an inner layer in accordance with a preferred method of manufacture.

As depicted in FIG. 14, a torque transfer layer 304 is then placed over the inner liner 302. In the case of a steerable introducer catheter, the flat wire assembly (not shown) may then be placed over the torque transfer layer 304. Alternatively, the flat wire assembly may be placed over an outer sheath 306. Another sheath layer (not shown) may additionally be placed over the flat wire assembly. The torque transfer layer terminates proximally of the distal end of the catheter.

Next, as depicted in FIG. 15, an outer sheath 306 is placed over the torque transfer layer 304 and may be made of either single or multiple sections of tubing that are either butted together or overlapped with each other. The multiple segments, or layers, of sheath material may be any length and/or hardness (durometer) allowing for flexibility of design. FIG. 15 identifies a plurality of segments, 322, 324, 326, 328 and 330. In this embodiment, the proximal end 330 of the outer sheath 306 may be made of a material such as nylon, and the remainder of the introducer may be made of one or more PEBAX materials. The lengths of the various segments may vary, but preferably, the durometer hardness levels will decrease as the outer sheath 306 approaches its distal end. For example, a nylon base may then be followed by one or more of the following PEBAX segments: 70D PEBAX; 60D PEBAX; 55D PEBAX; 40D PEBAX; 35D PEBAX; 30D PEBAX. The introducer shaft may also use one or more blends of the foregoing PEBAX materials, including, for example, 70D/60D PEBAX blend made by co-extrusion, or a 40D/35D PEBAX blend made by co-extrusion. Preferably, the various components of the outer sheath 306 according to this embodiment will be reflowed together during manufacturing. The proximal end of the shaft is preferably the longest segment, and more distal segments may preferably vary between 0.25" to 6", and more preferably from 0.25" to about 3". Preferably, the hardness levels of the segments and the lengths of the segments may be adjusted for specific applications, and preferably, the distal end may have the lowest durometer levels of all segments. The shaft segments may be selected to improve flexibility, torqueability, and pushability for the specific application, as appreciated by one of ordinary skill in the art. Alternatively, the catheter may be formed by placing a thin inner jacket or layer (e.g., PTFE layer) onto a mandrel (e.g., stainless steel mandrel) or extruding a thin inner jacket or layer (e.g., PEBAX layer) onto an extrusion mandrel (e.g., acetal mandrel), forming a torque transfer layer over the inner layer, and extruding an outer jacket or sheath (e.g., PEBAX jacket) over the torque transfer layer.

Lastly, a heat shrink layer 308 is placed over the assembled introducer assembly prior to reflow lamination. The heat shrink layer 308 is preferably a fluoropolymer or polyolefin material, such as FEP, or other suitable material as appreciated by one of ordinary skill in the art.

After assembly of the various components, the introducer assembly 300 is subjected to a reflow lamination process. FIG. 11 depicts a cross sectional view of the introducer assembly after this reflow process. Introducer assembly 1200 may be laminated by heating the assembly until the material comprising the outer sheath 1206 flows and redistributes around the circumference. Preferably, the heat shrink layer 1208 has a higher melt temperature than the outer sheath 1206, and during the melt process, the heat shrink layer 1208 retains its tubular shape and forces the liquefied sheath layer material 1206 into the torque transfer layer 1204 and into contact with the flat wires 1210/preformed tubes 1212 (if present) and the inner liner 1202. The introducer assembly 1200 may then be cooled. The mandrel is preferably left in place during the cooling process as it helps the introducer assembly to retain its inner lumen of at least about 6 French. The heat shrink layer 1208 may be left on the introducer assembly 1200, or optionally removed. If the heat shrink layer 1208 is removed, the outer sheath 1206 becomes the outside layer of the introducer catheter 1200.

Figure 16:
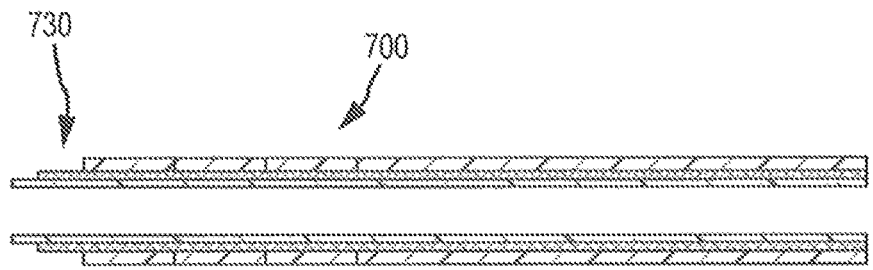
FIG. 16 depicts the components of an introducer assembled over a reflow mandrel assembly having a distal configuration for a tip assembly.
Figure 17:
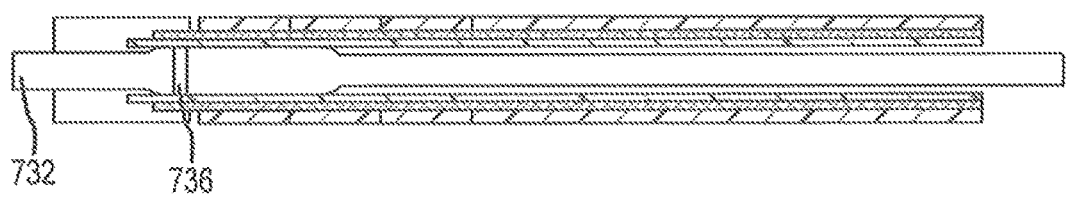
FIG. 17 depicts a tip component, having a radiopaque marker, attached to the distal end of the introducer depicted in FIG. 16.
Figure 18:
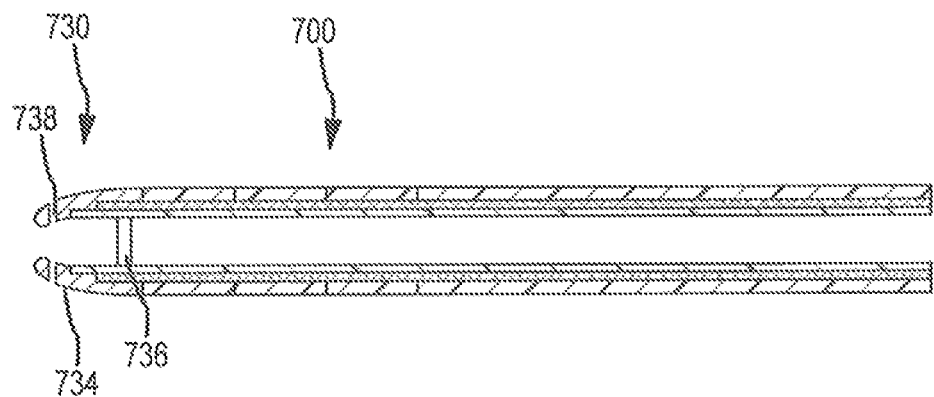
FIG. 18 depicts another tip component, having a radiopaque marker, attached to the distal end of the introducer depicted in FIG. 16.

Additionally, as shown in FIGS. 16-18, the present invention contemplates the inclusion of a tip assembly for use in medical procedures, such as an atraumatic tip, including, for example, a radiopaque material contained therein for location of the tip during use. For example, FIGS. 16-18 depict a cross section of an introducer catheter 700 having a distal portion 730 configured to accept a tip assembly 732 or 734. In both examples, the tip 732 or 734 includes a ring 736, e.g., a radiopaque marker, for location of the tip 732 or 734 during use. Additionally, FIG. 18 further includes a tip assembly 734 configured with a plurality of port holes 738 for delivery of, for example, irrigation fluid. The tip assembly may further be configured with ablation electrodes (not shown) operably connected to a power supply (not shown), for use in cardiac ablation procedures.

Although several embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A shaft for a steerable catheter, comprising:
a body including a circumferential wall defining an inner lumen, wherein the inner lumen is at least about 10 French, wherein the body comprises a first section of a first material and a second section of a second material, wherein the first section is bonded to the second section, and wherein the melting point of the first material differs from the melting point of the second material;
a flexible tube extending through the circumferential wall of the body;
a flat pull wire extending through the circumferential wall of the body, wherein at least a portion of the flat pull wire is disposed within the flexible tube and the flexible tube has a cross-sectional shape that differs from a cross sectional shape of the flat pull wire;
a pull ring circumferentially surrounding the outside of the first material, wherein the pull ring comprises a slot configured to accommodate the flat pull wire, wherein the slot extends through a wall of the pull ring; and
a wire reinforcing assembly embedded within the circumferential wall of the body, the wire reinforcing assembly comprising at least two flat wires braided into a wire mesh.

2. The shaft according to claim 1, wherein the melting point of the body differs from the melting point of the flexible tube.

3. The shaft according to claim 1, wherein the second section surrounds the first section.

4. The shaft according to claim 1, wherein the pull ring is embedded within the circumferential wall of the body, and further wherein the flat pull wire is welded to the pull ring slot.

5. The shaft according to claim 1, wherein the flexible tube comprises a first flexible tube and a second flexible tube, each extending through the circumferential wall of the body, and wherein the flat pull wire comprises a first flat pull wire and a second flat pull wire, each extending through the circumferential wall of the body with a portion of the first flat pull wire extending through the first flexible tube and a portion of the second flat pull wire extending through the second flexible tube.

6. The shaft according to claim 5, wherein the first flexible tube and the second flexible tube are spaced 180 degrees apart from each other about the circumferential wall of the body.

7. The shaft according to claim 1, wherein the at least two flat wires are from about 0.003 inches thick by about 0.007 inches wide.

8. The shaft according to claim 1, wherein the at least two flat wires are from at least about 0.004 inches thick and are at least about 0.012 inches wide.

9. The shaft according to claim 8, wherein the density of the wire mesh is from about 15 to about 70 pixels per inch.

10. The shaft according to claim 1, wherein the melting point of the first material is greater than the melting point of the second material.

11. A shaft for a steerable catheter, comprising:
a body including a circumferential wall defining an inner lumen, wherein the body comprises an inner layer and an outer layer bonded to the inner layer;
a steering assembly embedded in the body, the steering assembly comprising:
 a flexible tube extending longitudinally through the body radially outside of the inner layer;
 a flat pull wire extending longitudinally through the body radially outside of the inner layer, a portion of the flat pull wire being encased within the flexible tube; and
 a pull ring located radially outside of the inner layer and including two flow holes, wherein the flow holes are spaced about 180 degrees apart around the pull ring, the flat pull wire being secured to the pull ring, wherein the pull ring circumferentially surrounds the inner layer, and further wherein the pull ring comprises at least one slot configured to accommodate the flat pull wire, wherein the slot extends through a wall of the pull ring;
wherein a cross-sectional shape of the flexible tube differs from a cross-sectional shape of the flat pull wire; and
a reinforcing assembly embedded in the body radially outside of the inner layer, wherein the reinforcing assembly comprises a plurality of flat wires braided into a mesh,
wherein the outer layer is bonded to the inner layer through interstices in the mesh of the reinforcing assembly and the flow holes in the pull ring.

12. The shaft according to claim 11, wherein the flexible tube of the steering assembly comprises:
 a first flexible tube extending longitudinally through the body radially outside of the inner layer;
 a second flexible tube extending longitudinally through the body radially outside of the inner layer and positioned diametrically opposite the first flexible tube;
wherein the flat pull wire of the steering assembly comprises:
 a first flat pull wire extending through the body radially outside of the inner layer, a portion of the first flat pull wire being encased within the first flexible tube; and
 a second flat pull wire extending through the body radially outside of the inner layer, a portion of the second flat pull wire being encased within the second flexible tube,
wherein the first and second flat pull wires are secured to the pull ring, and wherein a cross-sectional shape of each flat pull wire differs from a cross-sectional shape of its respective flexible tube.

* * * * *